United States Patent
Gupta

(10) Patent No.: US 10,105,051 B2
(45) Date of Patent: Oct. 23, 2018

(54) SYSTEM AND METHOD FOR A PORTABLE EYE EXAMINATION CAMERA

(71) Applicant: SPECT INC., Palo Alto, CA (US)

(72) Inventor: Satish Chander Gupta, New Delhi (IN)

(73) Assignee: Spect Inc., Palo Alto, CA (US)

( * ) Notice: Subject to any disclaimer, the term of this patent is extended or adjusted under 35 U.S.C. 154(b) by 0 days.

(21) Appl. No.: 15/076,824

(22) Filed: Mar. 22, 2016

(65) Prior Publication Data

US 2016/0338587 A1 Nov. 24, 2016

Related U.S. Application Data

(60) Provisional application No. 62/136,609, filed on Mar. 22, 2015.

(51) Int. Cl.
| | |
|---|---|
| A61B 3/14 | (2006.01) |
| A61B 3/103 | (2006.01) |
| A61B 3/12 | (2006.01) |
| G02B 13/00 | (2006.01) |
| G02B 27/28 | (2006.01) |
| A61B 5/00 | (2006.01) |

(52) U.S. Cl.
CPC .............. *A61B 3/1208* (2013.01); *A61B 3/14* (2013.01); *A61B 5/6898* (2013.01); *G02B 13/003* (2013.01); *G02B 27/288* (2013.01); *A61B 2560/0431* (2013.01)

(58) Field of Classification Search
CPC ........... A61B 3/14; A61B 3/0025; A61B 3/12; A61B 3/102; A61B 3/0058
USPC ................................................ 351/200–246
See application file for complete search history.

(56) References Cited

U.S. PATENT DOCUMENTS

| | | | |
|---|---|---|---|
| 5,008,865 | A | 4/1991 | Shaffer et al. |
| 5,543,816 | A | 8/1996 | Heacock |
| 7,048,379 | B2 | 5/2006 | Miller et al. |
| 7,499,588 | B2 | 3/2009 | Jacobs et al. |
| 7,561,191 | B2 | 7/2009 | May et al. |
| 8,743,194 | B2 | 6/2014 | Fletcher et al. |
| 8,789,695 | B2 | 7/2014 | Mason |
| 9,154,594 | B2 | 10/2015 | Fletcher et al. |
| 9,325,884 | B2 | 4/2016 | Fletcher et al. |

(Continued)

FOREIGN PATENT DOCUMENTS

| | | |
|---|---|---|
| WO | WO-2015/054672 A1 | 4/2015 |
| WO | WO-2017/180965 A1 | 10/2017 |

OTHER PUBLICATIONS

Advanced Photonix, Inc. (2006). CdS Photoconductive photocells—PDV-P8001, 1 total page.

(Continued)

*Primary Examiner* — Mohammed Hasan
(74) *Attorney, Agent, or Firm* — Cooley LLP

(57) ABSTRACT

A system and method for a portable eye examination camera is described herein. The system and method may include: a light source disposed within said portable camera at a set distance away from an eye of a patient; a first lens within said portable camera for focusing the light from said light source onto a retina of the eye and providing a wide field retinal image; a second lens for receiving said retinal image and causing a magnification of said retinal image; and a digital camera within a mobile computing device for recording said retinal image.

37 Claims, 2 Drawing Sheets

(56) References Cited

U.S. PATENT DOCUMENTS

| | | | |
|---|---|---|---|
| 9,357,920 | B2 | 6/2016 | Yates et al. |
| 9,398,851 | B2 | 7/2016 | Anand et al. |
| 9,523,845 | B2 | 12/2016 | Fletcher et al. |
| 2003/0208125 | A1 | 11/2003 | Watkins |
| 2007/0280677 | A1 | 12/2007 | Drake et al. |
| 2008/0278686 | A1 | 11/2008 | Kasper et al. |
| 2012/0287255 | A1* | 11/2012 | Ignatovich ............ A61B 3/1208 348/78 |
| 2013/0028591 | A1 | 1/2013 | Hicks |
| 2013/0083185 | A1 | 4/2013 | Coleman, III |
| 2013/0128223 | A1* | 5/2013 | Wood ................... A61B 1/0019 351/206 |
| 2014/0055736 | A1 | 2/2014 | Ishak |
| 2014/0285766 | A1* | 9/2014 | Kohn Bitran ............ A61B 3/14 351/206 |
| 2016/0007008 | A1 | 1/2016 | Molgaard et al. |
| 2016/0066783 | A1 | 3/2016 | Kislinger et al. |
| 2016/0296111 | A1 | 10/2016 | Russo |
| 2016/0296112 | A1 | 10/2016 | Fletcher et al. |
| 2017/0055831 | A1 | 3/2017 | Miwa et al. |
| 2017/0126943 | A1 | 5/2017 | Fletcher et al. |
| 2017/0160533 | A1 | 6/2017 | Fletcher et al. |
| 2017/0161892 | A1 | 6/2017 | Tellatin et al. |

OTHER PUBLICATIONS

D-Eye smartphone-based retinal imaging system (2018), 7 total pages.
Guangzhou MeCan Medical (2017). High definition ophthalmic equipment non mydriatic portable digital fundus camera, 4 total pages.
Haddock, L.J. et al. (2013). "Simple, inexpensive technique for high-quality smartphone fundus photography in human and animal eyes," 2013, 5 total pages.
Haddock, L.J. et al. (2016). "Teleophthalmology of retinal diseases—Updates on telemedicine for diabetic retinopathy screening and smartphone funduscopy," *Retinal Physician* 8 total pages.
Jain, D. et al. (2016). "Open-source, ultra-low cost smartphone attachment for non-mydriatic fundus photography—Open indirect ophthalmoscope," ARVO Annual Meeting Abstract, Sep. 2016, 3 total pages.
Jin, K. et al. (2017). "Telemedicine screening of retinal diseases with a handheld portable non-mydriatic fundus camera," *BMC Ophthalm.* 2017, 7 total pages.
Peek Eye Care (2018). Peek Eye Care Overview, 6 total pages.
Russo, A. et al. (2015). "A novel device to exploit the smartphone camera for fundus photography," *J. Ophthalm.* 2015, 5 total pages.
Ryan, M.E. et al. (2015). "Comparison Among Methods of Retinopathy Assessment (CAMRA) Study: Smartphone, Nonmydriatic, and Mydriatic Photography," *Ophthalm.* 122:2038-2043.
Shen, B.Y. et al. (2017). "A portable, inexpensive, nonmydriatic fundus camera based on the Raspberry Pi® Computer," *J. Ophthalm.* 2017, 5 total pages.
Smartphone Ophthalmoscope and smartphone retinal camera (2018), 11 total pages.
International Search Report dated Jul. 13, 2018, for PCT Application No. PCT/US2018/029886, filed on Apr. 27, 2018, 4 pages.
International Search Report dated Aug. 3, 2018, for PCT Application No. PCT/US2018/033029, filed on May 16, 2018, 2 pages.
Miller, M. (2016). "Smartphone Dual Camera Showdown: Two Cameras, different focus," located at https://www.zdnet.com/article/smartphone-dual-camera-showdown-two-cameras-different-focus/, 7 total pages, no date.
Written Opinion of the International Searching Authority dated Jul. 13, 2018, for PCT Application No. PCT/US2018/029886, filed on Apr. 27, 2018, 10 pages.
Written Opinion of the International Searching Authority dated Aug. 3, 2018, for PCT Application No. PCT/US2018/033029, filed on May 16, 2018, 4 pages.

* cited by examiner

SYSTEM AND METHOD FOR A PORTABLE EYE EXAMINATION CAMERA

CROSS-REFERENCE

The present application claims benefit of the Provisional Application, Ser. No. 62/136,609, entitled "PORTABLE INDIRECT OPHTHALMOSCOPY BASED FUNDUS CAMERA for ROP SCREENING" filed on Mar. 22, 2015, which is herein incorporated by reference in its entirety.

DESCRIPTION WITH REFERENCE TO DRAWINGS

For a more complete understanding of the present invention, including its features and advantages, reference is now made to the detailed description of the invention taken in conjunction with the accompanying drawing in which.

DETAILED DESCRIPTION OF INVENTION

Figure 1:
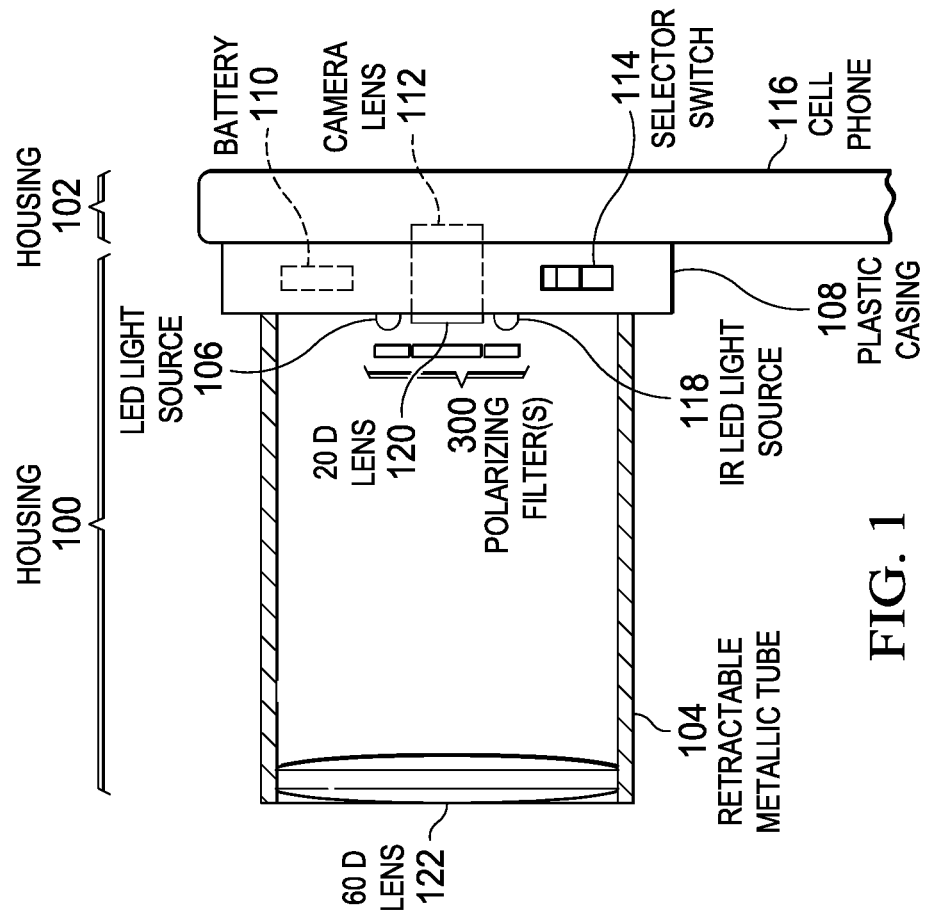
FIG. 1 shows the various components of the present invention.

While the making and using of various embodiments of the present invention are discussed in detail below, it should be appreciated that the present invention provides many applicable inventive concepts that may be embodied in a wide variety of specific contexts. The specific embodiments discussed herein are merely illustrative of specific ways to make and use the invention and do not delimit the scope of the invention.

There are many diseases that affect the retina. Normally, an examination of the retina is effected by an ophthalmoscope. The basic requirement of an ophthalmoscope, whether it be direct or indirect, is to illuminate the retina, which can then be focused onto the eye of an examining doctor. The focusing of the illuminated retina is effected by a system of lenses provided in the ophthalmoscope. An ophthalmoscope may be a direct or indirect. With a direct ophthalmoscope, the images are erect, magnified and virtual. In Indirect ophthalmoscope, the images formed are inverted, small or less magnified and real. A disadvantage associated with direct ophthalmoscope is that it does not have a wide field.

Fundus or retinal cameras which get a wide field of view, presently known in the art have a circular source of light besides the lens system. A disadvantage associated with such a camera is that the source of light touches the periphery of the cornea. In another known camera, the source of light comprises an Ultra Violet source, which touches the globe of the eye. Both of such known cameras are contact cameras having the distinct advantage of a wide field of view of the retina. However, a disadvantage associated with such known cameras is that of the contact between the eye and the light source. Such a contact could result in transmission of infection and chances of causing injury to the eye. Yet another disadvantage is that the magnification is small.

In order to obviate the aforesaid disadvantage, it is known to provide a direct ophthalmoscope fundus or retinal camera. In such a known camera, and in order to improve the quality of the images and to avoid reflexes, the optical system incorporated in the camera is complex and bulky. Such cameras are heavy equipment and cannot be easily moved after installation, hence cannot be used for field work. Further such non-contact fundus cameras have a field of view ranging from 15° to 60°. This is inadequate for photographing the periphery of retina, which is essential for recording the changes of retinopathy of prematurity.

Another method currently used in the field includes a retinal camera having an illumination source and an optical system for projecting the light onto a retina under examination. The camera further includes a filter means disposed substantially conjugate to the retina of the eye so as to illuminate the eye. The filter means includes at least one filter member with a disc shaped transmitting base plates, a first and second circular semi-transmitting surface. However, this system's a camera has a complicated illumination optical means.

In contrast, the present invention improves several aspects of the current systems and method used in field. One embodiment of the present invention relates to a retinal or fundus camera. Specifically, the retinal or fundus camera of the present embodiment is adapted to provide a photo documentation of the retina of the eye.

One aspect of this invention includes a retinal or fundus camera that is portable.

Another aspect of this invention includes a retinal or fundus camera, which has a wide field.

Another aspect of this invention includes a retinal or fundus camera, which does not contact the eye.

Another aspect of the invention includes a retinal camera, which can take pictures of retina in un-dilated pupil (4 to 5 mm size).

Another aspect of this invention includes a retinal or fundus camera, which has a simple optical system.

Another aspect of this invention includes a retinal or fundus camera, which is efficient.

One embodiment of the present invention includes a retinal or fundus camera which includes: a light source (e.g. Light Emitting Diode (LED)) within the camera and placed close to the camera lens and away from the eye of a patient to illuminate the retina of the patient's eye. The embodiment also includes: an Infra-Red LED within the camera and placed close to the camera lens and away from the eye of a patient to illuminate the retina of the patient's eye, without initiating the light reflex—thus keeping the pupil dilated for photographing the retina when a white LED flashes. In addition, the embodiment also includes: a 60 to 90 Diopter lens for receiving the reflection light from the retina and forming a real and magnified image of the retina. Moreover, the embodiment also includes: a 20 Diopter lens in front of the camera lens to provide further magnification of the retinal image. The embodiment further includes a portable computing device for recording the image.

In accordance with this invention, the first lens could have a high power of (e.g. such as 60 to 90) diopters—the greater the power of the lens translates to a larger the field of view. Further, such a lens comprises a biconvex aspherical lens. In this embodiment, the second lens has a power less than that of the first lens (e.g. such as 20 to 30 diopters), so as to provide a greater magnification of the retinal image and to act as a close up lens for the camera. Such a lens is usually a biconvex achromatic lens.

Thus, according to the present embodiment, the lens system has a varying power of (e.g. such as 20 to 90) Diopters. As the power of the lens increases, the field becomes wider but with less magnification. Thus, in this embodiment, the first lens has a higher power (e.g. such as 60 to 90 D), so that the field of view increases. However, the power of the first lens in this embodiment is not higher than 90 diopters, as the lens would then be too close to the eyeball under examination. Conversely, a magnification of the image is achieved by the second lens in this embodiment. Accordingly, the distance between the first and second lens is the sum of the focal length of the first and second lens.

Figure 2:
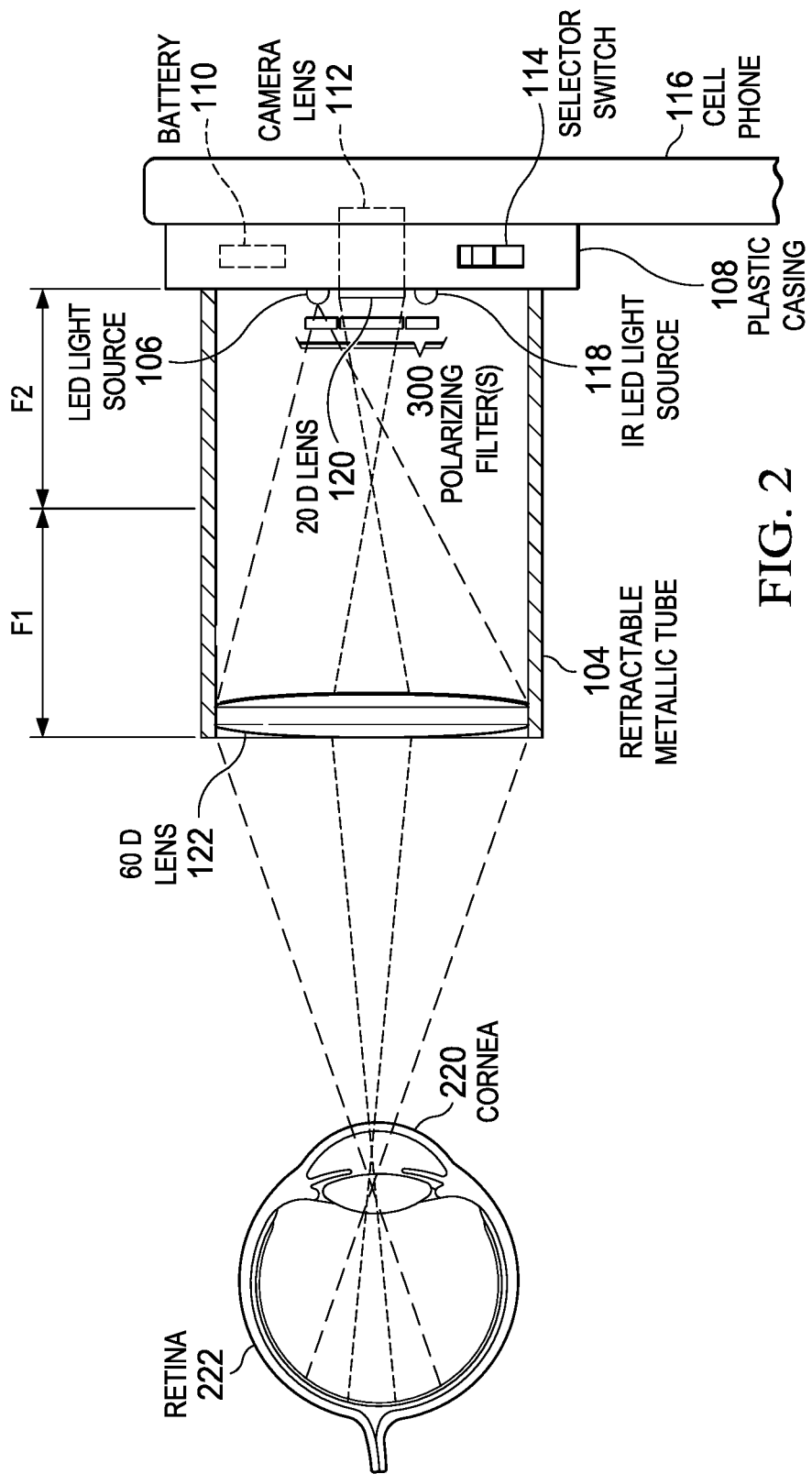
FIG. 2 shows another illustrations of the optical system of the present invention.

Now referring to FIGS. 1 and 2, Housing 100 includes of a re-tractable metallic tubular extension 104 that holds a 60 Diopter Lens 122 and 20 Diopter Lens 120 and a plastic casing 108. A light source 106, an Infra-Red light source 118 and Selector switch 114 and a power source battery 110 is disposed within the plastic casing 108.

In addition, the embodiment also includes three polarizing filters 300. A first filter is placed in front of the white light LED 106 and a second one is placed in front of 20 D magnifying lens 120. A third filter is also placed in front of the IR LED light source 118 similarly to the one placed in front of the white light LED source 106. Moreover, the second filter is placed at 90 degree polarity in respect to the first and third filters.

In addition, Housing 102, in this embodiment, is a digital camera combined in a cell phone 116. Moreover, the fundus camera has an optical system including of LED light source 106 and Infra-Red light source 118 connected to the power source battery 110. Furthermore, the Selector Switch 114 allows switching between LED light source 106 and Infra-Red LED 118. The light from either light source 106, 118 is focused onto a retina 222 of a patient through lens 122. As described herein above, this lens 122 has a high power such as 60 to 90 diopters, so as to provide a wide field of view for example, up to 110°. Further, lens 122 receives the image of the retina 222 at its focal point F1, which is then transmitted to a second lens 120 having a power less than that of lens 122. Thus, lens 120 acts as a magnifying lens and a close up lens for the camera. Accordingly, the image is at the focal length of lens 120, which is greater than the focal length of lens 122.

Moreover, the light from light source 106 or 118 is disposed such that it is almost coaxial with the receiving optics.

The above embodiments show using an alternative light source other than using the light source (e.g. normal flash light used in most digital cameras) within, or adjacent to, the cell phone. These unique aspect allows near alignment of projected light with the optical axis off the lenses. In addition, the present invention contemplates using any other portable computing device as a controller for the optical system, and not restricted to just a digital camera or cell phone. Further, although this embodiment shows a somewhat singular tube, the present invention is not restricted to a particular version of a tube and includes any type of retracting metallic tube.

Although this invention has been described with reference to an illustrative embodiment, this description is not intended to limit the scope of the invention. Various modifications and combinations of the illustrative embodiments as well as other embodiments of the invention will be apparent to persons skilled in the art upon reference to the description. It is therefore intended that the appended claims accomplish any such modifications or embodiments.

I claim:

1. A portable camera for capturing an image of a patient's eye without contacting the patient's eye, the portable camera comprising:
   a light source disposed within the portable camera;
   a first lens within the portable camera for focusing light from the light source onto a retina of the patient's eye and providing a wide-field retinal image, wherein the first lens is a biconvex aspherical lens;
   a second lens for receiving the wide-field retinal image and causing a magnification of the wide-field retinal image; and
   a digital camera within a mobile computing device for recording the magnified wide-field retinal image.

2. The portable camera as claimed in claim 1, wherein a LED is used as the light source, and wherein the LED is substantially coaxial with the first lens and the second lens.

3. The portable camera as claimed in claim 1, wherein an Infrared LED is used to illuminate the retina of the patient's eye without causing constriction of a pupil of the patient's eye.

4. The portable camera as claimed in claim 1, wherein a focal length of the second lens is greater than a focal length of the first lens.

5. The portable camera as claimed in claim 1, wherein a distance between the first lens and the second lens is a sum of focal lengths of the first and second lenses.

6. The portable camera as claimed in claim 1, wherein retinal photography is possible without dilating a pupil of the patient's eye.

7. A portable camera for capturing an image of a patient's eye without contacting the patient's eye, the portable camera comprising:
   a light source disposed within the portable camera;
   a first lens within the portable camera for focusing light from the light source onto a retina of the patient's eye and providing a wide-field retinal image;
   a second lens for receiving the wide-field retinal image and causing a magnification of the wide-field retinal image, wherein the second lens is a biconvex achromatic lens;
   a digital camera within a mobile computing device for recording the magnified wide-field retinal image.

8. The portable camera as claimed in claim 7, wherein a LED is used as the light source, and wherein the LED is substantially coaxial with the first lens and the second lens.

9. The portable camera as claimed in claim 7, wherein an Infrared LED is used to illuminate the retina of the patient's eye without causing constriction of a pupil of the patient's eye.

10. The portable camera as claimed in claim 7, wherein a focal length of the second lens is greater than a focal length of the first lens.

11. The portable camera as claimed in claim 7, wherein a distance between the first and second lens is a sum of focal lengths of the first and second lenses.

12. The portable camera as claimed in claim 7, wherein retinal photography is possible without dilating a pupil of the patient's eye.

13. A portable camera for capturing an image of a patient's eye without contacting the patient's eye, the portable camera comprising:
   a light source disposed within the portable camera;
   a first lens within the portable camera for focusing light from the light source onto a retina of the patient's eye and providing a wide-field retinal image;
   a second lens for receiving the wide-field retinal image and causing a magnification of the wide-field retinal image;
   a first polarizing filter placed in front of the light source;
   a second polarizing filter placed in front of second lens, wherein the second polarizing filter is placed at 90 degree polarity in respect to the first polarizing filter; and
   a digital camera within a mobile computing device for recording the magnified wide-field retinal image.

14. The portable camera as claimed in claim 13, wherein a LED is used as the light source, and wherein the LED is substantially coaxial with the first lens and the second lens.

15. The portable camera as claimed in claim 13, wherein an Infrared LED is used to illuminate the retina of the patient's eye without causing constriction of a pupil of the patient's eye.

16. The portable camera as claimed in claim 13, wherein a focal length of the second lens is greater than a focal length of the first lens.

17. The portable camera as claimed in claim 13, wherein a distance between the first and second lens is a sum of focal lengths of the first and second lenses.

18. The portable camera as claimed in claim 13, wherein retinal photography is possible without dilating a pupil of the patient's eye.

19. A portable camera for capturing an image of a patient's eye without contacting the patient's eye, the portable camera comprising:
   a light source disposed within the portable camera;
   a first lens within the portable camera for focusing light from the light source onto a retina of the patient's eye and providing a wide-field retinal image, wherein the first lens is a biconvex aspherical lens;
   a second lens for receiving the wide-field retinal image and causing a magnification of the wide-field retinal image, wherein a power of the first lens is greater than a power of the second lens; and
   a digital camera within a mobile computing device for recording the magnified wide-field retinal image.

20. The portable camera as claimed in claim 19, wherein a LED is used as the light source and wherein the LED is substantially coaxial with the first lens and the second lens.

21. The portable camera as claimed in claim 19, wherein an Infrared LED is used to illuminate the retina of the patient's eye without causing constriction of a pupil of the patient's eye.

22. The portable camera as claimed in claim 19, wherein a focal length of the second lens is greater than that a focal length of the first lens.

23. The portable camera as claimed in claim 19, wherein a distance between the first lens and the second lens is a sum of focal lengths of the first and second lenses.

24. The portable camera as claimed in claim 19, wherein retinal photography is possible without dilating a pupil of the patient's eye.

25. A portable camera for capturing an image of a patient's eye without contacting the patient's eye, the portable camera comprising:
   a light source disposed within the portable camera;
   a first lens within the portable camera for focusing light from the light source onto a retina of the patient's eye and providing a wide-field retinal image;
   a second lens for receiving the wide-field retinal image and causing a magnification of the wide-field retinal image, wherein the second lens is a biconvex achromatic lens, and wherein a power of the first lens is greater than a power of the second lens;
   a digital camera within a mobile computing device for recording the magnified wide-field retinal image.

26. The portable camera as claimed in claim 25, wherein a LED is used as the light source, and wherein the LED is substantially coaxial with the first lens and the second lens.

27. The portable camera as claimed in claim 25, wherein an Infrared LED is used to illuminate the retina of the patient's eye without causing constriction of a pupil of the patient's eye.

28. The portable camera as claimed in claim 25, wherein a focal length of the second lens is greater than a focal length of the first lens.

29. The portable camera as claimed in claim 25, wherein a distance between the first and second lens is a sum of focal lengths of the first and second lenses.

30. The portable camera as claimed in claim 25, wherein retinal photography is possible without dilating a pupil of the patient's eye.

31. A portable camera for capturing an image of a patient's eye without contacting the patient's eye, the portable camera comprising:
   a light source disposed within the portable camera;
   a first lens within the portable camera for focusing light from the light source onto a retina of the patient's eye and providing a wide-field retinal image;
   a second lens for receiving the wide-field retinal image and causing a magnification of the wide-field retinal image, wherein a power of the first lens is greater than a power of the second lens;
   a first polarizing filter placed in front of the light source;
   a second polarizing filter placed in front of the second lens, wherein the second polarizing filter is placed at 90 degree polarity in respect to the first polarizing filter; and
   a digital camera within a mobile computing device for recording the magnified wide-field retinal image.

32. The portable camera as claimed in claim 31, wherein a LED is used as the light source, and wherein the LED is substantially coaxial with the first lens and the second lens.

33. The portable camera as claimed in claim 31, wherein an Infrared LED is used to illuminate the retina of the patient's eye without causing constriction of a pupil of the patient's eye.

34. The portable camera as claimed in claim 31, wherein a focal length of the second lens is greater than a focal length of the first lens.

35. The portable camera as claimed in claim 31, wherein a distance between the first and second lens is a sum of focal lengths of the first and second lenses.

36. The portable camera as claimed in claim 31, wherein retinal photography is possible without dilating a pupil of the patient's eye.

37. A portable camera for performing retinal photography without dilating a pupil of an eye of a patient, the portable camera comprising:
   a LED light source disposed within the portable camera;
   two polarizing filters, wherein a first filter of the two polarizing filters is placed in front of the LED light source and a second filter of the two polarizing filters is placed in front of the second lens, wherein the second filter is placed at 90 degree polarity in respect to the first filter;
   a biconvex aspherical lens within the portable camera for focusing the light from the light source onto a retina of the eye of the patient and providing a wide field retinal image, whereby the LED light source focuses the wide field retinal image without causing constriction of the pupil of the eye of the patient;
   a biconvex achromatic lens for receiving the wide field retinal image and causing a magnification of the wide field retinal image, wherein a power of the biconvex aspherical lens is greater than a power of the biconvex achromatic lens, and wherein a focal length of the biconvex achromatic lens is greater than a focal length of the biconvex aspherical lens; and a digital camera within a mobile computing device for recording the magnified wide field retinal image.

* * * * *